United States Patent [19]

Misumi et al.

[11] 4,176,020
[45] Nov. 27, 1979

[54] PROCESS FOR ELECTROLYTIC DIMERIZATION OF N-SUBSTITUTED PYRIDINIUM SALT

[75] Inventors: Teruyuki Misumi; Susumu Furuhashi, both of Yokohama; Masaaki Shiga, Tokyo, all of Japan

[73] Assignee: Asahi Kasei Kogyo Kabushiki Kaisha, Osaka, Japan

[21] Appl. No.: 887,131

[22] Filed: Mar. 16, 1978

[30] Foreign Application Priority Data

Mar. 23, 1977 [JP] Japan .................................. 52/31108
Jan. 31, 1978 [JP] Japan .................................. 53/8959

[51] Int. Cl.$^2$ ............................................. C25B 3/10
[52] U.S. Cl. .................................................... 204/72
[58] Field of Search ...................... 204/72, 73 R, 59 R, 204/74

[56] References Cited

U.S. PATENT DOCUMENTS

| | | | |
|---|---|---|---|
| 3,488,267 | 1/1970 | Sloan | 204/73 A |
| 3,493,597 | 2/1970 | Campbell et al. | 204/73 A X |
| 3,717,646 | 2/1973 | Colchester et al. | 204/73 R UX |

Primary Examiner—F.C. Edmundson
Attorney, Agent, or Firm—Armstrong, Nikaido, Marmelstein & Kubovcik

[57] ABSTRACT

A novel process for the preparation of an N,N'-disubstituted tetrahydro-4,4'-bipyridyl by electrolytic dimerization of the corresponding N-substituted pyridinium salt, characterized in that, using a system including an electrolytic cell having at least one diaphragm and an extractor disposed outside the electrolytic cell, the electrolytic dimerization is carried out while an aqueous catholyte containing the corresponding N-substituted pyridinium salt is circulated between the electrolytic cell and the extractor in which the product is extracted into an extraction solvent, followed by separation of the aqueous phase which alone is recycled into the electrolytic cell. According to the process of the present invention, the electrolytic dimerization can be continued stably for a long time, a high current efficiency can be attained and the desired product can be obtained in high yield.

8 Claims, 6 Drawing Figures

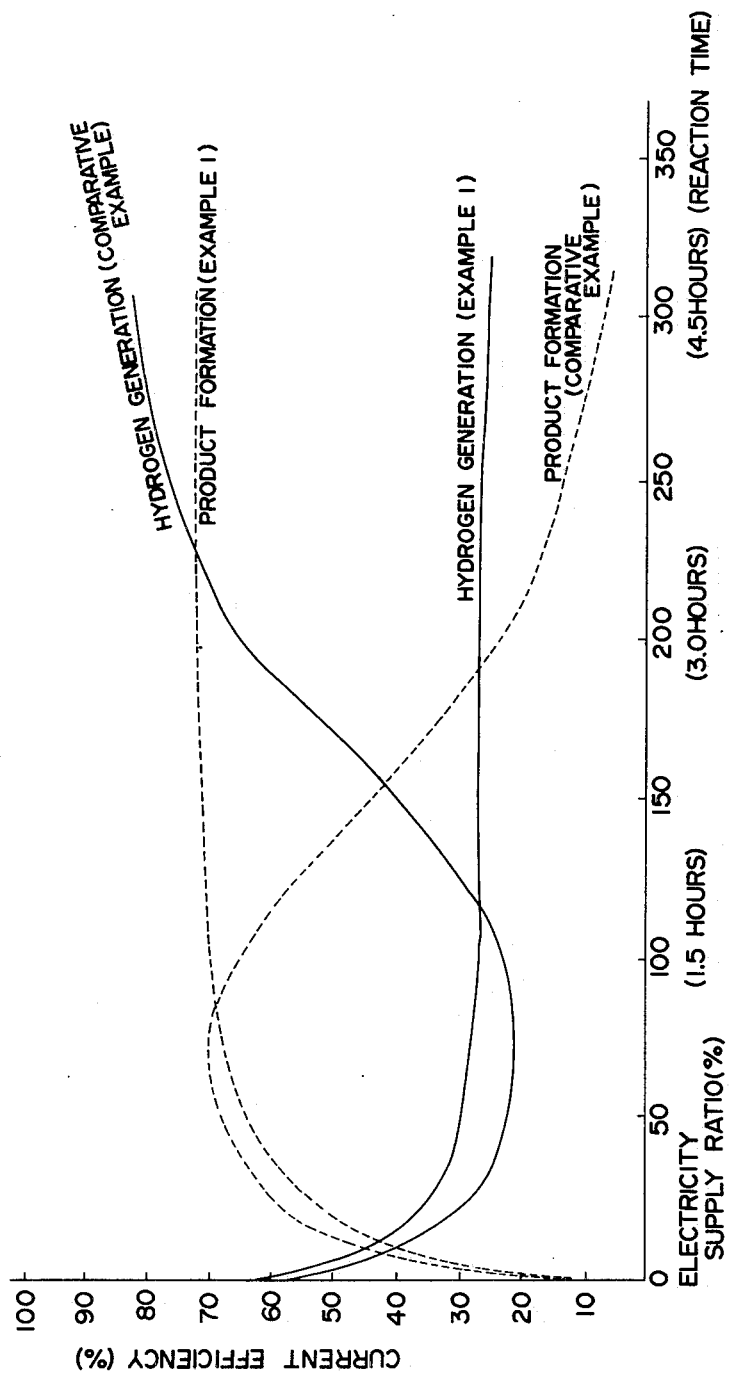

PROCESS FOR ELECTROLYTIC DIMERIZATION OF N-SUBSTITUTED PYRIDINIUM SALT

The present invention relates to a process for the preparation of an N,N'-disubstituted tetrahydro-4,4'-bipyridyl, and more particularly to an improved process for the preparation of an N,N'-disubstituted tetrahydro-4,4'-bipyridyl from the corresponding N-substituted pyridinium salt by electrolytic dimerization thereof.

It is known that an N,N'-disubstituted-4,4'-bipyridilium salt prepared by oxidizing an N,N'-disubstituted tetrahydro-4,4'-bipyridyl is a very effective herbicide. This compound is ordinarily prepared from 4,4'-bipyridyl by quaternization reaction but can also be obtained in high yield by oxidizing an N,N'-disubstituted tetrahydro-4,4'-bipyridyl with an organic oxidizing agent such a quinone or an inorganic oxyacid anhydride such as $SO_2$.

It is one and a principal object of the present invention to provide an excellent process for preparing an N,N'-disubstituted tetrahydro-4,4'-bipyridyl useful as a starting compound for the manufacture of an N,N'-disubstituted-4,4'-bipyridilium salt.

It is known in the art to prepare an N,N'-disubstituted tetrahydro-4,4'-bipyridyl (hereinafter often referred to as "dimer") by electrolytic reduction of an N-substituted pyridinium salt (hereinafter often referred to as "monomer salt").

Also, it is known that in order to prevent the product from accumulating in the electrolysis zone in electrolysis of an aqueous solution of the monomer salt, the electrolytic reduction is carried out in the presence of a water-immiscible organic solvent. For example, Japanese Patent Application Publication No. 186/1974 discloses that the oily product formed on the surface of the electrode is dissolved into and removed by a water-immiscible organic solvent, whereby the reaction can effectively proceed.

However, when we traced the process of Japanese Patent Application Publication No. 186/1974 by using the electrolytic process, it was found that since substances of unknown composition were deposited on the surface of the electrode and the current efficiency for formation of the dimer was rapidly lowered, it was impossible to continue the operation for a long time. It is believed as the reason that even if the water-immiscible organic solvent can dissolve and remove the dimer formed on the surface of the electrode, since the dimer dissolved in the solvent is always caused to be in contact with the surface of the electrode, some undesirable consecutive side reactions take place following the formation of the dimer and the effect of removal of the dimer from the electrode surface is lowered substantially and drastically.

As a result of extensive researches on a process for advantageously producing an N,N'-disubstituted tetrahydro-4,4'-bipyridyl by electrolytic dimerization of the corresponding N-substituted pyridinium salt on an industrial scale, we found out a novel process in which the foregoing defect accompanying the conventional process can be overcome and the electrolytic reaction can be continued stably for a long time.

More specifically, in accordance with the present invention, there is provided a process for the preparation of an N,N'-disubstituted tetrahydro-4,4'-bipyridyl by electrolytic dimerization of the corresponding N-substituted pyridinium salt, which process is characterized by the steps of:

(1) flowing an aqueous catholyte containing an N-substituted pyridinium salt through an electrolytic cell having an anode, a cathode and at least one diaphragm disposed between the anode and the cathode at its cathode chamber, said electrolytic cell being connected, through a circulation passage comprising a transferring passage and a feeding passage, with an extractor disposed outside said electrolytic cell, while applying electric current between said anode and said cathode, thereby to form an N,N'-disubstituted tetrahydro-4,4'-bipyridyl corresponding to said N-substituted pyridinium salt on the surface of the cathode and simultaneously remove said bipyridyl from the surface of the cathode into the aqueous catholyte flowing through the electrolytic cell;

(2) transferring the aqueous catholyte containing said bipyridyl to the extractor through the transferring passage and contacting said aqueous catholyte containing said bipyridyl with a water-immiscible organic solvent in said extractor to extract said bipyridyl into said organic solvent;

(3) separating the resulting aqueous phase from the resulting organic phase;

(4) feeding the separated aqueous phase alone back to the electrolytic cell through the feeding passage; and (5) continuously repeating the steps (1), (2), (3) and (4).

The process of the present invention may be batchwise conducted or may be continuously conducted while continuously or step-wise supplying the starting material, i.e. monomer salt. According to the process of the present invention, the contact of the resulting dimer with the surface of the cathode can be markedly restrained, and hence the occurrence of the consecutive side reactions of the resulting dimer can be effectively prevented. Therefore, according to the process of the present invention, it is possible to continue the electrolytic reaction stably for a long time. In the process of the present invention, removal, into the catholyte, of the oily product formed on the surface of the electrode is believed to be mainly attributed to the shear force generated by the rapid flow of the aqueous catholyte. Also, it is conceivable that the solubility of the oily product in water may be increased due to the function of the N-substituted pyridinium salt as a surface-active agent.

The foregoing and other objects, features and advantages of the present invention will be apparent to those skilled in the art from the following detailed description and appended claims taken in connection with the accompanying drawings in which:

FIG. 6 is a graph of the current efficiency against the electricity supply ratio which will be explained later with respect to Comparative Example and Example 1, shown together with current loss due to generation of hydrogen gas.

Figure 1:
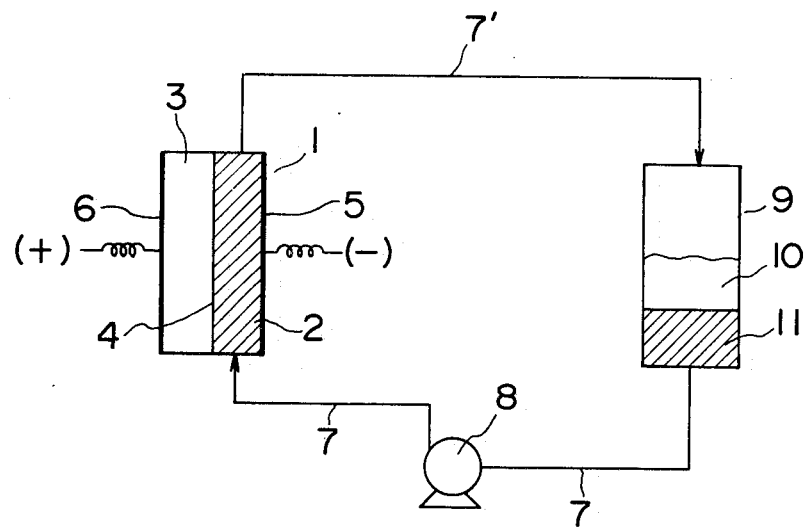
FIG. 1 is a diagrammatic view of the system showing one mode of the process of the present invention in which a two-chamber electrolytic cell is used.

One embodiment of the process of the present invention will now be described by reference to the accompanying drawings. Referring to FIG. 1, there is shown a system that is used for practicing the process of the present invention. In FIG. 1, reference numeral 1 designates an electrolytic cell including a cathode chamber 2, an anode chamber 3, a diaphragm 4, a cathode 5 and an anode 6. Reference numerals 7 and 7' respectively designate a feeding passage and a transferring passage, which cooperate with each other to constitute a circulation passage. Reference numerals 8 and 9 designate a catholyte-circulating means and an extractor, respectively. Reference numerals 10 and 11 designate an organic phase and an aqueous phase, respectively.

Water and a water-immiscible organic solvent capable of dissolving the dimer are charged in the extractor, and a predetermined amount of the monomer salt is dissolved in the aqueous phase. Only this aqueous phase containing the monomer salt (hereinafter referred to as "aqueous catholyte" or only as "catholyte") is continuously fed into the cathode chamber 2 through the feeding passage 7 by the catholyte-circulating means 8. This catholyte is continuously discharged from the outlet of the cathode chamber and is returned to the extractor 9 through the transferring passage 7'. When a predetermined voltage is applied between the anode and the cathode while the aqueous catholyte is thus circulated, the corresponding current is caused to flow between the two electrodes, and while the aqueous catholyte flows through the cathode chamber, a part of the monomer salt dissolved in the catholyte undergoes electrolysis. Although the resulting dimer has a property that it tends to cling to the electrode metal surface, since the aqueous catholyte flows vigorously along the surface of the electrode metal, the dimer is readily removed from the surface of the electrode. The dimer is then transferred to the extractor together with the catholyte. In the extractor, the dimer is extracted with the extraction solvent. While the foregoing steps of operations are continuously repeated, the monomer salt in the catholyte is gradually converted to the dimer.

When the linear velocity of the aqueous catholyte flowing along the surface of the cathode is too low, the efficiency of removal of the product from the cathode surface is lowered and hence the product is deposited on the cathode surface, resulting in lowering of the electrolysis efficiency. The linear velocity of the aqueous catholyte necessary for effectively conducting electrolysis varies depending on the quantity of electricity supplied, but when the electrolysis is carried out at a current density of 0.1 to 40 A/dm$^2$, it is preferred to flow the aqueous catholyte at a linear velocity of at least 0.1 m/sec. The upper limit of the linear velocity is not particularly critical, but practically 10 m/sec. Although it is technically possible to flow the aqueous catholyte at a linear velocity of over 10 m/sec, it is not preferred to employ too high a linear velocity, because the increase of a liquid pressure at the inlet of the electrolytic cell not only requires the electrolytic cell components such as the diaphragm to have a high pressure strength but also necessitates use of a high pressure-resistant circulating pump, and also because the electrolysis performance is saturated at above a certain linear velocity. The preferred linear velocity is generally within the range of from 0.3 to 5 m/sec.

The extraction solvent may somtimes be dissolved in the aqueous catholyte. The quantity of the extraction solvent contained in the aqueous catholyte varies depending on the kind of the solvent used, but the smaller the quantity of the contained solvent, the better the obtained results are. But, it is noted that even extraction solvents having a water solubility of 0.1 to 5% can be used in the present invention without trouble. However, when an organic solvent that may be dissolved in the aqueous catholyte at a concentration of more than about 10% by weight is employed, the obtained results are extremely poor. The reason is considered to be as follows.

The reaction product is dissolved and contained, at least at an equilibrium concentration in extraction, in the after-extraction aqueous catholyte to be recycled from the extractor to the electrolytic cell. However, when a solvent having a high water solubility is used, the solubility of the reaction product in the aqueous catholyte is enhanced and hence, a large quantity of the reaction product is contained in the aqueous catholyte to be fed back from the extractor to the electrolytic cell. Accordingly, a considerable amount of the reaction product is always present on the surface of the electrode and therefore, undesirable consecutive side reactions of the reaction product are caused to occur, and the resulting by-products are deposited on the surface of the electrode, leading to the unfavorable surface conditions of the electrode.

In the above-mentioned embodiment, the diaphragm 4 serves not only to cause the anion of the monomer salt to migrate into the anode chamber so that the anion from the aqueous catholyte is removed, but also to prevent the resulting dimer from diffusing into the anode chamber so as to prevent the reaction product from being brought into contact with the anode.

As the preferred monomer salt that may be electrolytically dimerized in the process of the present invention, there can be mentioned N-($C_1$–$C_5$) alkylpyridinium salts such as N-methylpyridinium salts, N-ethylpyridinium salts, N-n- and-isopropylpyridinium salts, N-n-,-iso-,sec- and -tert-butylpyridinium salts, N-n-,-iso-,-sec-,-active- and -tert-amylpyridinium salts. The process of the present invention is also applicable to the case where an N-($C_1$–$C_5$) alkylpyridinium salt having such a substituent bonded to the pyridine nucleus as a halogen atom, a $C_1$–$C_5$ alkyl group, a hydroxyl group or an amino group is electrolytically dimerized. As the anion of the above-mentioned N-alkylpyridinium salts, there can be mentioned, a chloride ion, a bromide ion, an iodide ion, a fluoride ion, a sulfate group, a benzenesulfonate group, a $C_1$–$C_{30}$ alkylsulfonate group, a trifluoromethanesulfonate group, a methylsulfate group, a benzoate group, an acetate group, a citrate group, a lactate group, a fumarate group, a malate group, a maleate group, a salicylate group, a succinate group, a trichloroacetate group, a phosphate group, a cyanide group, a thiocyanate group, a nitrate group, a carbonate group, a fluorosilicate group, a tetrafluoroborate group and the like. A halide ion such as a chloride ion and a bromide ion, a sulfate group and a methylsulfate group are especially preferred as the anion. For example, N-methylpyridinium chloride is prepared by the reaction between pyridine and methyl chloride. An N-methylpyridinium salt having other anion as mentioned above is prepared, for example, by adsorbing it on a cation exchange resin and treating it with an acid having the above-mentioned anion followed by recovery of the resulting N-methylpyridinium salt. Such N-substituted pyridinium salt may be fed to the aqueous catholyte in the form of a powder or an aqueous solution. It is preferred that the purity of the starting monomer salt be as high as possible. If impurities such as methanol and aromatic nitro compounds which may react with the formed N,N'-disubstituted tetrahydro-4,4'-bipyridyl are incorporated in the starting monomer salt, the electrolysis is adversely affected drastically.

As the organic solvent that may be used as an extraction solvent in practicing the process of the present invention, there can be mentioned, for example, saturated chain hydrocarbons such as n-pentane, n-hexane, n-heptane, n-octane, n-nonane, n-decane, isopentane, isohexane, isoheptane, isooctane, petroleum ether, gasoline and kerosine; cycloaliphatic hydrocarbons such as cyclopentane, cyclohexane, methylcyclohexane, cyclohexene and 1,3-cyclohexadiene; aromatic hydrocarbons such as benzene, toluene, xylenes, ethylbenzene, propylbenzenes, methylethylbenzenes, styrene, cumene, hemimellitene, pseudocumene and mesitylene; halogenated aromatic compounds such as chlorobenzene, dichlorobenzenes, chlorotoluenes, bromobenzene and fluorobenzene; aromatic amines such as aniline, N-Methylaniline, N-ethylaniline, dimethylanilines, diethylanilines, toluidines and chloroanilines; aromatic cyano compounds such as benzonitrile; ethers such as diethyl ether, diisopropyl ether, di-n-butyl ether, di-n-hexyl ether, methyl phenyl ether, ethyl phenyl ether, ethyl benzyl ether, furan and 2-methylfuran; water-immiscible alcohols having 4 or more carbon atoms such as butyl alcohols, amyl alcohols, heptanols and hexanols; and amines such as triethylamine and triamylamines. They may be used alone or in mixture.

These organic solvents have a capacity of dissolving the dimer and are immiscible with water, and therefore, any of them can be used as the extraction solvent. Of these organic solvents, aromatic hydrocarbons such as toluene, xylenes and ethylbenzene, halogenated aromatic compounds such as chlorobenzene, and saturated chain hydrocarbons such as n-hexane and isooctane are preferred. The term "water-immiscible" as used herein is defined to mean that a solvent is insoluble or even if soluble it is soluble in water only at a concentration as low as 10% by weight or less.

In the present invention, extraction can be accomplished using any of known liquid-liquid extractors such as rotary disc contactors, cross counter type centrifugal extractors, packed towers, spray towers, perforated (sieve) plate towers, baffle towers and mixer-settlers.

The electrode materials that can be used for practicing the process of the present invention will now be described. As the cathode, there can be used metallic materials having a high hydrogen overvoltage, such as lead, mercury, copper, alloys containing at least one of these metals as a main component, e.g., lead-tellurium alloys, lead-silver alloys, lead-tin alloys and lead-copper alloys. As the anode, there can be used electrically conductive materials having resistance to the corrosive action of the electrolyte, such as platinum, carbon, nickel, titanium and stainless steel.

The surface conditions of the cathode are one of especially important factors in the present invention. In order to obtain good results, it is required to always keep the cathode surface clean and flat. When such requirements of the surface conditions of the electrode are not satisfied, the supplied electricity tends to be consumed, in the majority, for the generation of hydrogen. Therefore, close attention should be paid to the surface conditions of the electrode.

As a diaphragm for partitioning the electrolytic cell, there can be used inorganic membranes such as an asbestos membrane and a glass filter; porous organic membranes made of polymeric compounds such as cellophane, cellulose acetate, polyacrylonitrile and polytetrafluoroethylene; and ion exchange resin membranes. But in the present invention, ion exchange resin membranes which have a high selectivity to ionic species are especially preferred. Advantages of the use of an ion exchange resin membrane reside in that the product, i.e., the dimer, can be perfectly prevented from being decomposed by the action of, for example, $Cl_2$ or $O_2$ which is formed by anodic oxidation of an anion($Cl^-$ or $SO_4^{--}$) of the N-substituted pyridinium salt and in that anionic species gradually accumulated in the cathode chamber with continuation of electrolysis can be easily removed outside the dimerization reaction zone. Moreover, the use of the ion exchange resin membrane makes it possible that unfavorable impurities contained in the starting monomer salt are not present in the electrolytic dimerization zone.

In case ion exchange resin membranes are employed in practicing the process of the present invention, the kind and number of the ion exchange resin membrane and the combination thereof in the case where the number of the membrane is two or more are determined according to various conditions such as the kind and purity of a starting monomer salt. Usually, the satisfactory results are obtained with the use of one to three of ion exchange resin membranes.

When the electrolytic cell is partitioned by two of ion exchange membranes and divided into a cathode chamber, an anode chamber and an intermediate chamber, it is preferred that electrolyte solutions for the respective chambers be circulated separately and the electrolyte concentration in each electrolyte solution be controlled constantly to a certain level by removing the dissolved electrolyte or adding the electrolyte afresh. For example, when the anion exchange resin membrane and the cation exchange resin membrane are disposed on the cathode side and on the anode side, respectively, and the N-substituted pyridinium salt is fed into the catholyte, an anion of the N-substituted pyridinium salt, e.g., chloride ion, is electrically transferred through the anion exchange resin membrane into the intermediate chamber and accumulated therein, while the N,N'-disubstituted tetrahydro-4,4'-bipyridyl formed by electrolytic dimerization is removed outside the reaction zone by extraction. On the other hand, when, for example, an alkali electrolyte such as sodium hydroxide is employed in the anolyte, the alkali metal ion such as sodium ion is transferred through the cation exchange resin membrane into the intermediate chamber, while the hydroxide ion is oxidized at the anode to generate oxygen. In the intermediate chamber, the sodium ion as an example reacts with the chloride ion to form sodium chloride. Accordingly, the concentration of sodium chloride in the intermediate chamber liquid increases with continuation of electrolysis. Therefore, it is preferred to replace the intermediate chamber liquid with water little by little and thereby remove sodium chloride in order to maintain the sodium chloride concentration constant. On the hand, since sodium hydroxide in the anolyte is consumed, it is preferred to supply sodium hydroxide little by little into the anolyte.

As the electrolyte which may be employed in practicing the process of the present invention, there can be mentioned, for example, hydroxides such as sodium hydroxide, potassium hydroxide, lithium hydroxide and ammonium hydroxide; metallic salts such as lithium chloride, lithium bromide, lithium fluoride, lithium sulfate, lithium phosphate, potassium chloride, potassium bromide, potassium fluoride, potassium sulfate, potassium phosphate, sodium chloride, sodium bromide, sodium fluoride, sodium sulfate, sodium phosphate, calcium chloride, calcium bromide, copper sulfates, aluminum sulfate and sodium nitrate; ammonium salts such as ammonium chloride and ammonium sulfate. They may be used alone or in combination. Of these electrolytes, sodium hydroxide, sodium chloride and sodium sulfate are most preferred.

A variety of methods for practicing the process of the present invention with the use of the ion exchange resin membrane are conceivable, but many factors such as current efficiency and resistances of the ion exchange resin membrane to gases to be generated which factors have significant influences on practicing the process of the present invention must be taken into consideration. From the above point of view, the most preferred embodiment of electrolytic dimerization of the present invention is as follows.

In accordance with this embodiment, there is provided a process for the preparation of an N,N'-disubstituted tetrahydro-4,4'-bipyridyl by electrolytic dimerization of the corresponding N-substituted pyridinium salt, which process is characterized by the steps of:

(1) flowing an aqueous catholyte containing an N-substituted pyridinium salt through an electrolytic cell having an anode and a cathode which are disposed opposite to each other, and a cation exchange resin membrane on the anode side and an anion exchange resin membrane on the cathode side which are disposed without contacting each other and substantially in parallel with the anode and the cathode, said anode, said cathode, said cation exchange resin membrane and said anion exchange resin membrane cooperating with the inner wall of the electrolytic cell to provide an anode chamber, an intermediate chamber and a cathode chamber in the cell, said electrolytic cell being connected, through a circulation passage comprising a transferring passage and a feeding passage, with an extractor disposed outside said electrolytic cell, while applying electric current between said anode and said cathode, thereby to form an N,N'-disubstituted tetrahydro-4,4'-bipyridyl corresponding to said N-substituted pyridinium salt on the surface of the cathode and simultaneously remove said bypyridyl from the surface of the cathode into the aqueous catholyte flowing through the electrolytic cell;

(2) transferring the aqueous catholyte containing said bipyridyl to the extractor through the transferring passage and contacting said aqueous catholyte containing said bipyridyl with a water-immiscible organic solvent in said extractor to extract said bipyridyl into said organic solvent;

(3) separating the resulting aqueous phase from the resulting organic phase;

(4) feeding the separated aqueous phase alone back to the electrolytic cell through the feeding passage; and (5) continuously repeating the steps (1), (2), (3) and (4); said aqueous catholyte being constantly fed with the N-substituted pyridinium salt, said anode chamber being constantly fed with an alkali and the salt formed in the intermediate chamber by neutralization between the anion of the N-substituted pyridinium salt immigrated from the cathode chamber and the cation of said alkali immigrated from the anode chamber being constantly removed from said intermediate chamber.

Figure 5:
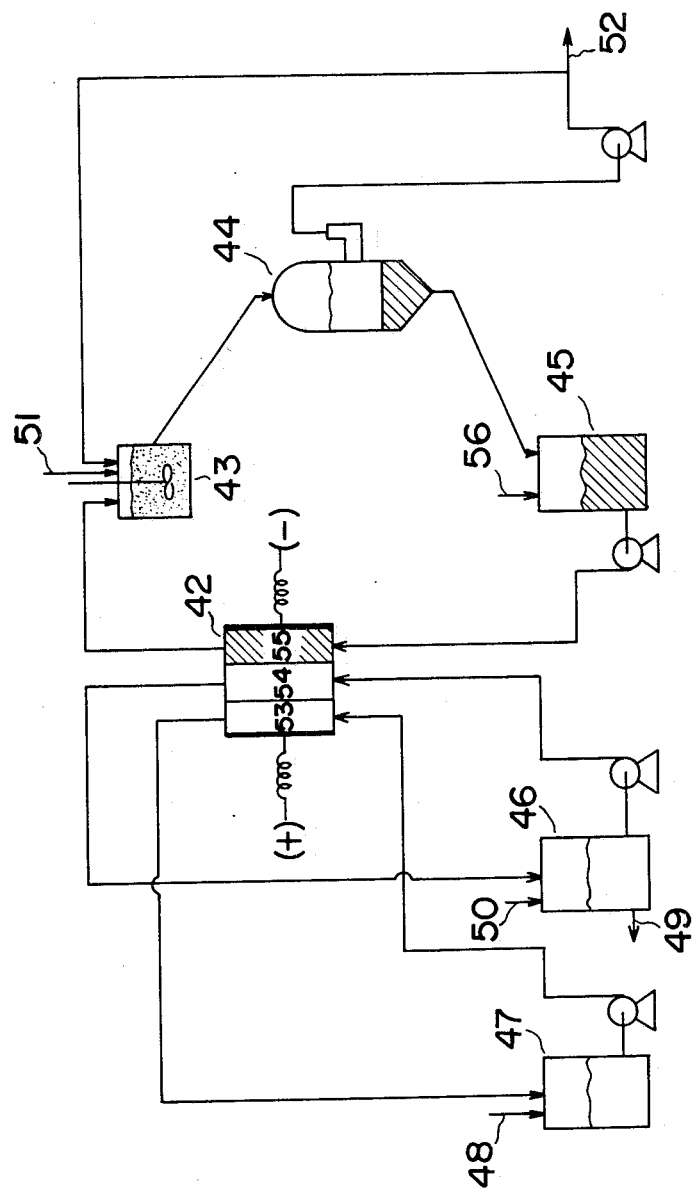
FIG. 5 is a diagrammatic view of the same system of the process of the present invention as shown in FIG. 3, illustrated in more detail.

This preferred embodiment of the present invention is practiced, for example, according to the system as shown in FIG. 5. In FIG. 5, reference numerals 42, 43, 44, 45, 46 and 47 designate an electrolytic cell, a mixer, a settler, a catholyte reservoir, an intermediate chamber liquid reservoir and an anolyte reservoir, respectively, and reference numerals 48, 49, 50, 51 and 52 designate an alkali inlet, an intermediate chamber liquid outlet, a water inlet, an extraction solvent inlet and a product outlet, respectively. The anode chamber 53 is connected, in series, with the anolyte reservoir 47 and in turn the circulating pump through the circulation passage. The intermediate chamber 54 is connected, in series, with the intermediate liquid reservoir 46 and in turn the circulating pump through the circulation passage. With these arrangements, the electrolytes in the anode chamber and the intermediate chamber can be individually circulated throughout electrolysis. The aqueous catholyte which has left the cathode chamber 55 is subjected to extraction of the product in the mixer 43, separated from the extract in the settler 44 and recycled via the catholyte reservoir 45 into the cathode chamber 55. A part of the extract is recycled into the mixer 51 and the residual part of the extract is withdrawn from the product outlet 52 continuously. While an alkali is continuously fed at the alkali inlet 48 into the anolyte reservoir 47, the N-substituted pyridinium salt is continuously fed from an N-substituted pyridinium salt inlet 56 into the catholyte reservoir 45 and the aqueous solution of the salt formed in the intermediate chamber is continuously withdrawn from the intermediate chamber liquid reservoir 46, whereby the requirement of the material balance can be met. The flows of the individual electrolytes passing through the anode chamber 53, the intermediate chamber 54 and the cathode chamber 55 may preferably be uniform. Therefore, the flows of the electrolytes in the above-mentioned chambers may preferably be adequately controlled by choosing optimum conditions with respect to the number, size, shape, arrangement etc. of the openings in the liquid inlets and the liquid outlets of the chambers.

The case where an aqueous N-methylpyridinium chloride solution is employed as an aqueous catholyte in practicing this preferred embodiment of electrolytic dimerization of the present invention will be explained by way of example in more detail. The N-methylpyridinium cation in the aqueous solution is given an electron on the surface of the cathode and dimerized to yield N,N'-dimethyltetrahydro-4,4'-bipyridyl. Although said bipyridyl is almost insoluble in water and tends to cling to the surface of the cathode, it is effectively removed therefrom by the circulating flow passing through the cathode chamber and introduced, together with the catholyte, into the extractor, where the bipyridyl is extracted into the extraction solvent.

Generally, the preferred concentration of N-methylpyridinium chloride in the aqueous catholyte may be 0.1 to 2 moles/liter, more preferably 0.5 to 1 mole/liter. When the concentration is more than 2 moles/liter, the amount of hydrogen generated in the electrolysis is small but the yield of the product is low. On the other hand, when the concentration is too low, namely less than 0.1 mole/liter, the yield is high but the amount of hydrogen generated tends to be large. (The preferred concentration as mentioned above generally applies to not only the so-called continuous method but also the batch-wise method irrespective of the kind of the monomer salt.)

The concentration of N-methylpyridinium chloride in the aqueous catholyte is maintained constant by continuous feed of new N-methylpyridinium chloride in an amount corresponding to that of the consumed N-methylpyridinium cation. The anion of N-methylpyridinium chloride, namely chloride ion, moves, through the anion exchange resin membrane, into the intermediate chamber, where it reacts with the alkali metal cation which has moved thereinto from the anode chamber, to form the salt. Since the concentration of the salt in the intermediate chamber gradually increases with continuation of electrolysis, the concentration may preferably be maintained constant by continuous replacement of the intermediate chamber liquid with water. As apparent from the above, the chloride anion does not reach the anode and therefore the formation of molecular chlorine does not occur. Even if any, since the cation exchange resin membrane having a high resistance to molecular chlorine is disposed on the anode side, the deterioration of the membrane does not occur. While the alkali metal cation of the alkali supplied to the anode chamber moves, through the cation exchange resin membrane, into the intermediate chamber, the remaining hydroxide ion thereof is oxidized at the anode to generate oxygen. Since the cation exchange resin membrane having a high resistance to oxygen in the nascent state is disposed on the anode side, the deterioration of the membrane does not occur as well.

Since the N-substituted pyridinium salt is directly fed into the aqueous catholyte in this preferred embodiment, the concentration of the N-substituted pyridinium salt in the catholyte can optionally be increased to a level as high as, e.g., above 1 mole/liter, whereby the electric resistance of the cathode chamber can be reduced, and the limiting current density in the cation exchange resin membrane which is low as compared with that in the anion exchange resin membrane does not determined the rate of electrolysis, so that the electrolysis can be conducted at a high current density. Other advantages of direct continuous feed of the N-substituted pyridinium salt into the catholyte reside in that, because there is involved no passage of the N-substituted pyridinium cation through the cation exchange resin membrane, the membrane voltage can be controlled to a low level and hence the cost of electrolysis can be reduced, and the current efficiency in the preparation of the N,N'-disubstituted tetrahydro-4,4'-bipyridyl can be enhanced.

In case the electrolytic dimerization of the N-substituted pyridinium salt is practiced according to this preferred embodiment, the mixing of the ionic species, for example, the N-substituted pyridinium cation and the cation of other electrolyte such as sodium ion does not occur in any of the anode chamber, the intermediate chamber and the cathode chamber and, therefore, the separation and removal of the indivisual electrolysis products can be very easily conducted.

As discussed above, in the electrolytic dimerization of the N-substituted pyridinium salt according to this preferred embodiment, not only can the high-yield preparation of the N,N'-disubstituted tetrahydro-4,4'-bipyridyl be attained, but also the stable continuous operation can be carried out for a long time without deteriorations of the ion exchange resin membranes and the like.

In the case where the process of the present invention is practiced on an industrial scale, when the starting monomer salt is continuously fed to the catholyte and the reaction product dissolved in the extraction solvent is continuously withdrawn, the operation of electrolytic dimerization can be continued stably for a long time.

The present invention will now be described in more detail by reference to the following Examples, which should not be construed to limit the scope of the present invention.

COMPARATIVE EXAMPLE

Figure 2:
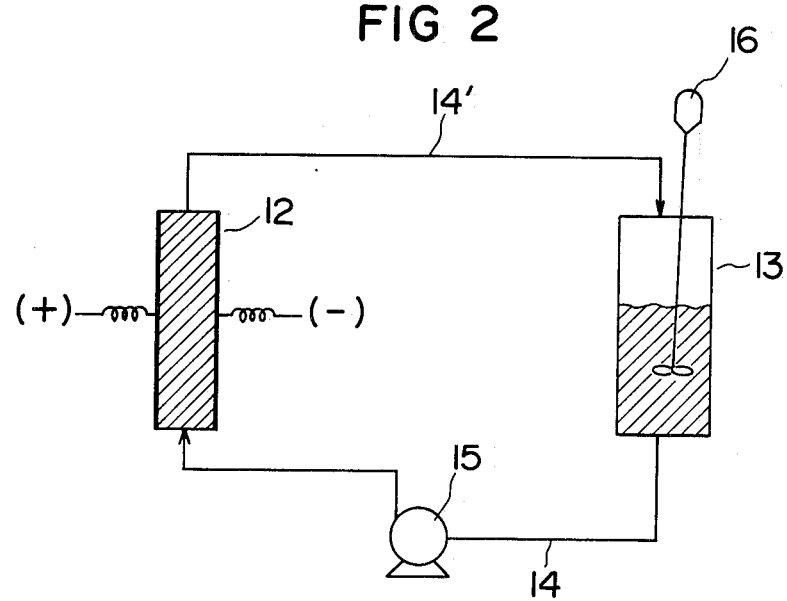
FIG. 2 is a diagrammatic view of the system showing the process of Comparative Example in which an aqueous catholyte and an organic solvent is only mixed and the resulting suspension is circulated.

An electrolytic cell including a platinum gauze as the anode and a lead plate having an effective electrode area of 2 cm×20 cm as the cathode and an agitation tank were connected through a circulation passage via a circulating pump as shown in FIG. 2. In FIG. 2, reference numerals 12 and 13 designate an electrolytic cell and an agitation tank, respectively, reference numerals 14 and 14' designate circulation passages, and reference numerals 15 and 16 designate a circulating pump and an agitator, respectively.

In the agitation tank 13 were charged 300 ml of an aqueous solution containing 0.1 mole of N-methylpyridinium chloride and 300 ml of diethyl ether. While the two liquids were homogeneously dispersed by vigorously agitating by means of the agitator 16, the dispersion was circulated at a linear velocity, in the electrolytic cell, of 0.5 m/sec between the agitation tank 13 and the electrolytic cell 12 through the circulation passages 14 and 14' by the circulating pump 15. While this circulation is maintained, an electric current of 2.8 amperes is flowed between the electrodes. Within several minutes from the state of the supply of electric current, a polymeric solid was accumulated on the surface of the electrode and the generation of hydrogen grew conspicuous. When the electrolysis was continued for 5 hours, it was found that about 82% of the total quantity of the supplied electricity were consumed for the generation of hydrogen.

EXAMPLE 1

Figure 3:
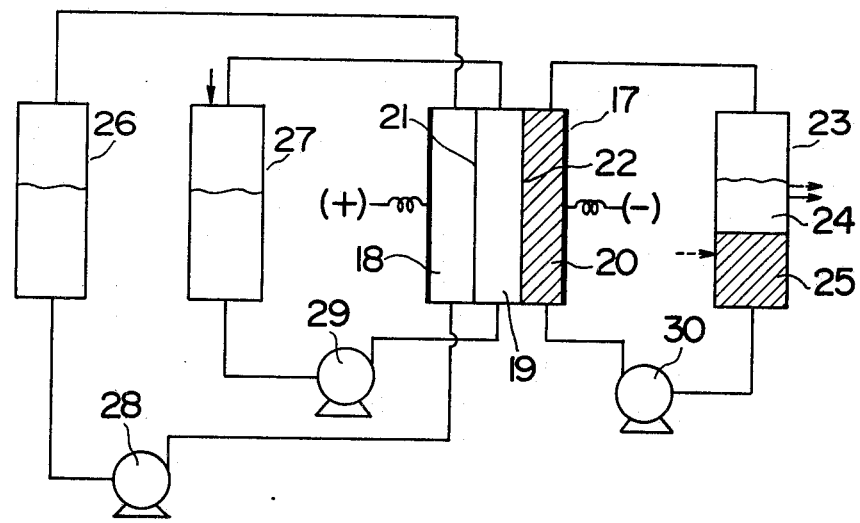
FIG. 3 is a diagrammatic view of the system showing another mode of the process of the present invention in which a three-chamber electrolytic cell is used.

An electrolytic cell including a platinum gauze as an anode and a lead plate having an effective electrode area of 2 cm×20 cm as a cathode was partitioned by an anion exchange resin membrane commercially available under the tradename "Aciplex A-101" (Asahi Kasei Kogyo K.K., Japan) on the anode side and a cation exchange resin membrane commercially available under the tradename "Nafion #415" (Du Pont Company, U.S.A.) on the cathode side to provide an anode chamber having a chamber width of 4 mm, an intermediate chamber having a chamber width of 15 mm and a cathode chamber having a chamber width of 1 mm in the electrolytic cell. This electrolytic cell was connected with an extractor and liquid reservoirs as shown in FIG. 3. In FIG. 3, reference numerals 17, 18, 19, 20, 21 and 22 designate an electrolytic cell, an anode chamber, an intermediate chamber, a cathode chamber, an anode exchange resin membrane and a cation exchange resin membrane, respectively, and reference numerals 23, 24, 25, 26 and 27 designate an extractor, an extraction solvent, an aqueous catholyte, an anolyte reservoir and an intermediate chamber liquid reservoir, respectively. Reference numerals 28, 29 and 30 designate liquid circulating pumps.

500 ml of a 1 N aqueous solution of N-methylpyridinium sulfate were charged in the intermediate chamber liquid reservoir 27, and 300 ml of a 0.1 N aqueous solution of N-methylpyridinium sulfate and 300 ml of n-hexane were charged in the extractor 23. Further, a 1 N aqueous solution of sodium sulfate was charged in an anolyte reservoir 26. These aqueous solutions were circulated by the circulating pumps 28, 29 and 30. The reaction product was removed from the catholyte by extraction in the extractor and only the aqueous phase of the lower layer in the extractor was circulated at a linear velocity, in the cathode chamber, of 0.5 m/sec. The linear velocities of the anolyte and the intermediate chamber liquid were both 0.1 m/sec in the anode chamber and in the intermediate chamber, respectively.

While the anolyte, the intermediate chamber liquid and the catholyte were thus circulated, an electric current of 7 amperes per $dm^2$ was flowed between the electrodes. The pH of the aqueous catholyte was about 7 just after the start of supply of the electric current, but it rose to about 13 in several minutes and this pH value did not change until the electrolysis was ended. The voltage between the electrodes was about 10 volts at the start of the electrolysis but it gradually decreased and it was 7.8 volts at the end of electrolysis. While the starting monomer salt solution was continuously fed into the intermediate chamber, all of the n-hexane layer in the extractor was replaced with 300 ml of fresh n-hexane 5 hours after the start of the electrolysis and the electrolysis was further continued for 5 hours.

After completion of the electrolysis, the resulting dimer dissolved in the n-hexane was analyzed by a nuclear magnetic resonance (NMR) analysis apparatus JNM-PMX 60 (trade name of an NMR apparatus manufactured and sold by Nihon Denshi Co., Ltd., Japan). It was found that 61.7% of the total quantity of electricity supplied were utilized for the formation of the dimer. From the quantity of hydrogen generated during the electrolysis, it was found that 37.4% of the total quantity of electricity supplied were consumed for the generation of hydrogen. The yield was 90.2% with respect to the consumed monomer salt.

This Example was compared with the above Comparative Example with respect to the current efficiency and the results are shown in FIG. 6. In FIG. 6, the term "electricity supply ratio" is intended to mean the quantity of the actually supplied electricity (expressed in terms of percent) taken relative to the theoretical quantity of electricity necessary for the electrolytic dimerization of all of the monomer salt charged at the start of the electrolysis which theoretical quantity is evaluated as 100%.

EXAMPLE 2

Using the same electrolysis system as used in Example 1, the electrolysis was carried out in the same manner as in Example 1 except that N-methylpyridinium chloride was used instead of N-methylpyridinium sulfate. 59.4% of the total quantity of electricity supplied were utilized for the dimerization and 39.2% of the total quantity of electricity supplied were consumed for the generation of hydrogen. The yield was 89.4% with respect to the consumed monomer salt.

EXAMPLE 3

In the same system as used in Example 1, a cation exchange resin membrane "Nafion #415" was used as the membrane for partitioning the anode chamber and the intermediate chamber and an anion exchange resin membrane "Aciplex A-101" was used as the membrane for partitioning the intermediate chamber and the cathode chamber, and a 1 N aqueous solution of N-methylpyridinium chloride as a starting monomer salt was fed directly to the cathode chamber. 300 ml of the 1 N aqueous solution of N-methylpyridinium chloride and 300 ml of diethyl ether were charged in the extractor 23, and 300 ml of a 1 N aqueous solution of sodium sulfate were charged in each of the anolyte reservoir 26 and the intermediate chamber liquid reservoir 27. These solutions were circulated by the circulating pumps 28, 29 and 30, and the electrolysis was conducted in the same manner as described in Example 1. The amount of the dimer obtained by the electrolysis for 10 hours corresponded to 58.6% of the total quantity of electricity supplied and the quantity of the electricity consumed for the generation of hydrogen was 41.0% of the total quantity of electricity supplied. The yield was 92.4% with respect to the consumed monomer salt.

EXAMPLE 4

Figure 4:
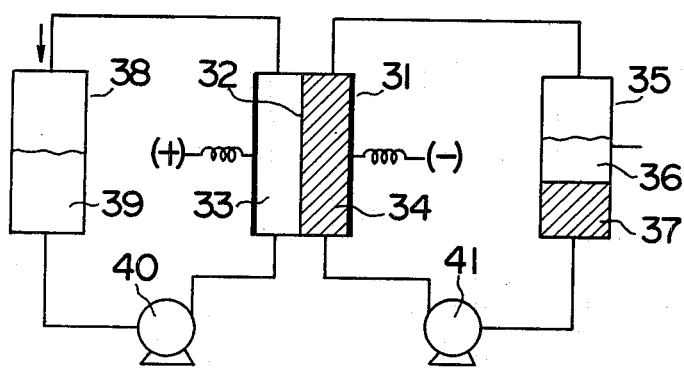
FIG. 4 is a diagrammatic view of the system showing still another mode of the process of the present invention in which a two-chamber electrolytic cell is used and an anolyte is also circulated.

An electrolytic cell including a platinum gauze as an anode and a lead plate having an effective electrode area of 2 cm×20 cm as a cathode was partitioned by a cation exchange resin membrane "Nafion #415" to provide an anode chamber and a cathode chamber, which were then connected with an anolyte reservoir and an extractor, respectively, each being disposed outside the electrolytic cell, as shown in FIG. 4. In FIG. 4, reference numerals 31, 32, 33 and 34 designate an electrolytic cell, a cation exchange resin membrane, an anode chamber and a cathode chamber, respectively, and reference numerals 35, 36, 37, 38 and 39 designate an extractor, an extraction solvent, an aqueous catholyte, an anolyte reservoir and an anolyte, respectively. Reference numerals 40 and 41 designate liquid circulating pumps.

500 ml of a 1 N aqueous solution of N-methylpyridinium sulfate were charged in the anolyte reservoir 38, and 300 ml of a 0.1 N aqueous solution of N-methylpyridinium sulfate and 300 ml of n-hexane were charged in the extractor 35. The anolyte was circulated between the anolyte reservoir and the anode chamber by the circulating pump 40 at a linear velocity, in the anode chamber, of 0.1 m/sec and the catholyte was circulated between the extractor and the cathode chamber by the circulating pump 41 at a linear velocity, in the cathode chamber, of 0.5 m/sec. While the liquids were thus circulated, an electric current of 2.8 amperes was flowed between the electrodes. After the start of supply of the electric current, N-methylpyridinium sulfate was continuously supplied little by little to the anolyte reservoir to make up for the consumed monomer salt, and 100 ml of the n-hexane containing the dimer were withdrawn and replaced with 100 ml of new n-hexane every two hours after the start of the electrolysis. The electrolysis could be continued for 10 hours.

After completion of the electrolysis, the dimer contained and dissolved in n-hexane was analyzed using the NMR analysis apparatus. It was found that 62.4% of the total quantity of electricity supplied were utilized for the formation of the dimer and 37.1% of the total quantity of electricity supplied were consumed for the generation of hydrogen. The yield was 93.8% with respect to the consumed monomer salt.

EXAMPLE 5

Referring to FIG. 5, an electrolytic cell including a platinum gauze as an anode and a plate of an alloy composed mainly of Pb and containing 0.5% by weight of tellurium as a cathode and having an effective electrode area of 2 cm×20 cm was partitioned by an anion exchange resin membrane "Aciplex A-101" on the cathode side and a cation exchange resin membrane "Nafion #415" on the anode side to provide a cathode chamber 55 having a chamber width of 1 mm, an intermediate chamber 54 having a chamber width of 15 mm and an anode chamber 53 having a chamber width of 4 mm. These chambers were each connected with an extractor and/or liquid reservoir through circulation passages via circulating pumps as shown in FIG. 5.

300 ml of an aqueous solution of sodium chloride having a concentration of 1 mole/liter, 300 ml of a 1 N aqueous solution of sodium hydroxide and 600 ml of an aqueous solution of N-methylpyridinium chloride having a concentration of 1 mole/liter were charged in an intermediate chamber liquid reservoir 46, an anolyte reservoir 47 and a catholyte reservoir 45, respectively. These aqueous solutions were each circulated by circulating pumps so that the linear velocities each were 0.1 m/sec in the intermediate chamber 54, 0.1 m/sec in the anode chamber 53 and 0.8 m/sec in the cathode chamber 55. As shown in FIG. 5, 1500 ml of toluene were charged in the upper layer of the settler 44 and circulated between the settler 44 and a mixer 43 at a rate of 100 ml/min by an extraction solvent-circulating pump. While the solutions were thus circulated, an electric current was flowed between the electrodes at a current density of 10 A/dm$^2$. With the lapse of time, N-methylpyridinium chloride in the catholyte was gradually converted into N,N'-dimethyltetrahydro-4,4'-bipyridyl, which was transferred into the extraction solvent. Accordingly, an aqueous solution of N-methylpyridimum chloride having a concentration of 3.1 moles/liter was continuously fed to the catholyte reservoir so that the concentration of N-methylpyridinium chloride in the catholyte was maintained at 1 mole/liter. On the other hand, a 5 N aqueous solution of sodium hydroxide was fed little by little to the anolyte reservoir so that the pH of the anolyte was maintained at about 13. Since sodium chloride was formed and gradually accumulated in the intermediate chamber, an intermediate chamber liquid was replaced little by little with pure water in the intermediate chamber liquid reservoir so that the concentration of sodium chloride was maintained at 1 mole/liter. The electrolysis was continued for 150 hours under the aforementioned conditions. It was found that 8.9% of the total quantity of the supplied electricity were consumed for the generation of hydrogen and 90.2% were used for the formation of N,N'-dimethyltetrahydro-4,4'-bipyridyl. The yield was 88.1% with respect to the consumed monomer salt.

EXAMPLE 6

An electrolytic cell including a platinum-deposited titanium plate as an anode and a copper plate as a cathode was partitioned by an anion exchange resin membrane "Aciplex A-101" on the cathode side and a cation exchange resin membrane "Nafion #415" on the anode side to provide a cathode chamber, an intermediate chamber and an anode chamber. The electrode area was 40 cm$^2$. This electrolytic cell was connected with an extractor through liquid circulation passages via a liquid circulating pump. 600 ml of diethyl ether were charged in the extractor. 1 liter of a 1 N aqueous solution of sodium sulfate and 1.5 liters of a 1 N aqueous solution of sodium chloride were charged in an anolyte reservoir and an intermediate chamber liquid reservoir, respectively. In the same manner as in the preceding Examples, these solutions were each circulated so that the linear velocities were 0.5 m/sec at each chamber. 700 ml of an aqueous solution of N-methylpyridinium chloride having a concentration of 9.4% by weight was charged in the extractor, and circulated by a circulating pump so that the linear velocity of this aqueous solution was 0.7 m/sec in the cathode chamber. While all the solutions were thus circulated, an electric current was flowed between the two electrodes at a current density of 20 A/dm$^2$.

A 2 N aqueous solution of sodium hydroxide was continuously fed to the anode chamber at a rate of 119 g/hr and an aqueous solution of NaCl was withdrawn from the intermediate chamber at a certain rate while supplying water, so that the concentrations of the solutions were maintained at initial levels throughout the electrolysis.

The electrolysis was continued for 8 hours under the above conditions. It was found that the conversion of the charged N-methylpyridinium chloride was 67.3%, and that 36.0% of the total quantity of the supplied electricity were used for the formation of N,N'-dimethyltetrahydro-4,4'-bipyridyl. The quantity of the electricity consumed for the generation of hydrogen was 42.5% of the total quantity of the supplied electricity on the average throughout the electrolysis. The yield was as high as 95.7% with respect to the consumed monomer salt.

After the electrolysis, the electrolytic cell was disassembled to examine the electrodes. It was found that the electrodes were not electrolytically corroded at all.

EXAMPLE 7

A platinum-plated titatnium gauze was used as an anode and a lead alloy plate in which about 0.5% by weight of tellurium was incorporated to enhance the hardness was used as a cathode. The effective electrode area of the lead alloy plate was 2 cm×20 cm. An electrolytic cell in the shape of a box was assembled. An anion exchange resin membrane "Aciplex A-101" was disposed on the cathode side and a cation exchange resin membrane "Nafion #415" was disposed on the anode side. The chamber widths of a cathode chamber, an intermediate chamber and an anode chamber were 1 mm, 15 mm and 4 mm, respectively. A pair of an inlet and an outlet each in the shape of a circular hole having a diameter of 6 mm for electrolytes were formed on each of the sides of the electrolytic cell, that is, on the lateral side of each of the cathode chamber and the anode chamber and on the top and the bottom of the intermediate chamber. This electrolytic cell was incorporated in a system as shown in FIG. 5 and the electrolysis was carried out under the following conditions.

The linear velocities of the circulating electrolytes were about 0.5 m/sec in the cathode chamber and about 0.1 m/sec in the intermediate and anode chambers. The quantity of the electrolyte charged in each liquid reservoir was 300 ml. N-Methylpyridinium chloride was dissolved in the catholyte at a concentration of 1 mole/liter, sodium chloride was dissolved in the intermediate chamber liquid at a concentration of 1 mole/liter and sodium hydroxide was dissolved in the anolyte at a concentration of 1 mole/liter. Throughout the electrolysis, N-methylpyridinium chloride and sodium hydroxide were fed to the catholyte and to the anolyte, respectively, at a rate of about 0.2 mole/hr, so that the aforementioned concentrations were maintained. The aqueous solution of sodium chloride was withdrawn from the intermediate chamber liquid reservoir at a rate of about 0.2 mole/hr in terms of the amount of sodium chloride and water was supplied instead. While the electrolytes were thus circulated, an electric current was flowed between the two electrodes at a current density of 20 amperes/dm$^2$. When the electrolysis was continued for 4 hours under the aforementioned conditions, it was found that 20.3% of the total quantity of the supplied electricity was consumed for the generation of hydrogen. This percentage gradually increased with continuation of the electrolysis, and when the electrolysis was continued for 26.5 hours, it was found that the percentage rose to about 40%.

As an extraction solvent was used 1.5 liters of toluene. Fresh toluene was not continuously supplied, but the extraction solvent was circulated at a rate of 100 ml/min between the settler and the mixer of a mixer-settler type extractor by a circulating pump. The stirrer of the mixer was rotated at about 500 rpm. At each of the intervals of 4 hours, 8.5 hours, 13 hours, 18 hours and 26.5 hours after the start of the electrolysis, the electrolysis operation was temporarily discontinued and all the toluene solution was replaced with fresh toluene. Of cource, at the end of the electrolysis, the toluene solution was only withdrawn and need not be replaced with fresh toluene. The amounts of N,N'-dimethyltetrahydro-4,4'-bipyridyl formed for the respective intervals were determined using the nuclear magnetic resonance analysis apparatus. It was found that the amounts formed for the respective intervals were 0.416 mole, 0.49 mole, 0.45 mole, 0.441 mole and 0.638 mole, respectively. These amounts of the formed N,N'-dimethyltetrahydro-4,4'-bipyridyl indicate consumptions of 69.7%, 73.0%, 67.1%, 59.1% and 50.3 %, respectively, of the respective quantities of the supplied electricity, for the formation of N,N'-dimethyltetrahydro-4,4'-bipyridyl.

The total amount, fed to the catholyte at the start of the electrolysis and throughout the electrolysis, of N-methylpyridinium chloride was 5.566 moles, and the amount of N-methylpyridinium chloride remaining in the catholyte after completion of the electrolysis was 0.519 mole. The total amount of the formed N,N'-dimethyltetrahydro-4,4'-bipyridyl was 2.435 moles. The yield was as high as 96.5% with respect to the consumed monomer salt. The total quantity of the supplied electricity was 2.537 faradays. Accordingly, it was found that 61.6% of the total quantity of the supplied electricity were utilized for the formation of N,N'-dimethyltetrahydro-4,4'-bipyridyl.

EXAMPLE 8

An electrolytic cell including a platinum gauze as an anode and a lead plate having an effective electrode area of 2 cm×20 cm as a cathode was partitioned by an anion exchange resion membrane "Aciplex A-101" on the anode side and a cation exchange resin membrane "Nafion #415" on the cathode side to provide an anode chamber having a chamber width of 4 mm, an intermediate chamber having a chamber width of 15 mm and a cathode chamber having a chamber width of 1 mm. The electrolytic cell was connected with an extractor and liquid reservoirs as shown in FIG. 3.

300 ml of an aqueous solution containing 1 mole/liter of sodium chloride were charged in the intermediate chamber liquid reservoir 27 and 300 ml of an aqueous solution containing 0.5 mole/liter of sodium hydroxide were charged in the anolyte reservoir 26. 1.5 liters of diethyl ether and 600 ml of an aqueous solution containing 0.2 mole/liter of N-methylpyridinium chloride were charged in an extractor 23. The respective aqueous solutions were circulated by circulating pumps 29, 28 and 30, respectively. Only the aqueous phase of the lower layer in the extractor was circulated at a linear velocity, in the cathode chamber, of 0.5 m/sec. The linear velocities of the anolyte and the intermediate chamber liquid were both 0.1 m/sec in the anode chamber and in the intermediate chamber, respectively.

While the anolyte, the intermediate chamber liquid and the catholyte were thus circulated, an electric current of 20 amperes/dm$^2$ was flowed between the electrodes. The voltage between the electrodes was about 18 volts at the start of the electrolysis, but dropped to about 11 volts after one hour. From 2 hours on after the start of the electrolysis, the voltage was stabilized at about 9.5 volts. N-Methylpyridinium chloride was supplied little by little into the catholyte so that the concentration thereof in the catholyte was maintained at 0.2 mole/liter. Sodium hydroxide was added little by little to the anolyte so that the pH value of the anolyte was maintained at about 13. When the concentration of N,N'-dimethyltetrahydro-4,4'-bipyridyl in diethyl ether reached 0.3 millimole/g, all the diethyl ether solution in the extractor was withdrawn and replaced with fresh diethyl ether. About 20% of the total quantity of the supplied electricity were consumed for the generation of hydrogen.

The electrolysis was further continued. The amount of hydrogen generated increased gradually with the lapse of the electrolysis time. 50 Hours after the start of the electrolysis, it was found that about 30% of the total quantity of the supplied electricity were consumed for the generation of hydrogen.

As a result of the electrolysis for 26.5 hours, 2.435 moles of N,N'-dimethyltetrahydro-4,4'-bipyridyl were obtained from 5.05 moles of N-methylpyridinium chloride. This yield was as high as 96.4% of the theoretical yield. 75.6% of the total quantity of the supplied electricity were utilized effectively.

After completion of the electrolysis, the electrolytic cell was disassembled. A small amount of a brown sludge-like matter was deposited on the surface of the cathode but this could be easily removed by washing with water. When the surface of the cathode was cleansed and then examined by a microscope, any deterioration and loss of the cathode due to corrosion was not observed.

What is claimed is:

1. A process for the preparation of an N,N'-disubstituted tetrahydro-4,4'-bipyridyl by electrolytic dimerization of the corresponding N-substituted pyridinium salt which process is characterized by the steps of:
   (1) flowing an aqueous catholyte containing an N-substituted pyridinium salt through an electrolytic cell having an anode, a cathode and at least one diaphragm disposed between the anode and the cathode at its cathode chamber at a linear velocity, in the cathode chamber, of at least 0.1 m/sec., said electrolytic cell being connected, through a circulation passage comprising a transferring passage and a feeding passage, with an extractor disposed outside said electrolytic cell, while applying electric current between said anode and said cathode, thereby to form an N,N'-disubstituted tetrahydro-4,4'-bipyridyl corresponding to said N-substituted pyridinium salt on the surface of the cathode and simultaneously remove said bipyridyl from the surface of the cathode into the aqueous catholyte flowing through the electrolytic cell;
   (2) transferring the aqueous catholyte containing said bipyridyl to the extractor through the transferring passage and contacting said aqueous catholyte containing said bipyridyl with a water-immiscible organic solvent in said extractor to extract said bipyridyl into said organic solvent;
   (3) separating the resulting aqueous phase from the resulting organic phase;
   (4) feeding the separated aqueous phase alone back to the electrolytic cell through the feeding passage; and
   (5) continuously repeating the steps (1), (2), (3) and (4).

2. A process for the preparation of an N,N'-disubstituted tetrahydro-4,4'-bipyridyl as claimed in claim 1, wherein said at least one diaphragm is an ion exchange resin membrane.

3. A process for the preparation of an N,N'-disubstituted tetrahydro-4,4'-bipyridyl as claimed in claim 1, wherein said electrolytic cell has two diaphragms which are respectively a cation exchange resin membrane disposed on the anode side and an anion exchange resin membrane disposed on the cathode side, thereby to provide an anode chamber, an intermediate chamber and a cathode chamber, and an anolyte is circulated between said anode chamber and an anolyte reservoir disposed outside the electrolytic cell, while circulating an intermediate chamber liquid between said intermediate chamber and an intermediate chamber liquid reservoir disposed outside the electrolytic cell.

4. A process for the preparation of an N,N'-disubstituted tetrahydro-4,4'-bipyridyl as claimed in claim 3, wherein said anolyte is an aqueous solution containing an alkali and said intermediate chamber liquid is an aqueous solution containing the same salt as that to be formed by neutralization between the anion of the N-substituted pyridinium salt and the cation of said alkali.

5. A process for the preparation of an N,N'-disubstituted tetrahydro-4,4'-bipyridyl as claimed in any of claims 1 to 4, wherein the continuous repetition of the steps (1), (2), (3) and (4) is conducted while supplying the N-substituted pyridinium salt directly or indirectly into the cathode chamber.

6. A process for the preparation of an N,N'-disubstituted tetrahydro-4,4'-bipyridyl as claimed in any of claims 1 to 5, wherein said organic solvent is toluene.

7. A process for the preparation of an N,N'-disubstituted tetrahydro-4,4'-bipyridyl as claimed in any of claims 1 to 6, wherein said cathode is made of a metallic material selected from the group consisting of lead, copper and alloys containing lead and/or copper as a main component.

8. A process for the preparation of an N,N'-disubstituted tetrahydro-4,4'-bipyridyl as claimed in any of claims 1 to 7, wherein said N-substituted pyridinium salt is N-methylpyridinium chloride.

* * * * *